United States Patent
Fix et al.

(10) Patent No.: US 9,640,682 B2
(45) Date of Patent: May 2, 2017

(54) DEVICE FOR EMITTING ELECTROMAGNETIC RADIATION

(71) Applicant: Robert Bosch GmbH, Stuttgart (DE)

(72) Inventors: Richard Fix, Gerlingen (DE); Patrick Sonstroem, Herrenberg (DE); Gottfried Doehler, Erlangen (DE)

(73) Assignee: Robert Bosch GmbH, Stuttgart (DE)

( * ) Notice: Subject to any disclaimer, the term of this patent is extended or adjusted under 35 U.S.C. 154(b) by 123 days.

(21) Appl. No.: 14/315,462

(22) Filed: Jun. 26, 2014

(65) Prior Publication Data
US 2015/0001425 A1    Jan. 1, 2015

(30) Foreign Application Priority Data

Jun. 28, 2013 (DE) .................. 10 2013 212 640

(51) Int. Cl.
*G01N 21/31*    (2006.01)
*H01L 31/0232*    (2014.01)

(52) U.S. Cl.
CPC ....... *H01L 31/02325* (2013.01); *G01N 21/31* (2013.01); *G01N 2201/062* (2013.01); *G01N 2201/0612* (2013.01)

(58) Field of Classification Search
CPC ........... G01N 21/31; G01N 2201/0612; G01N 2201/062; G01S 1/00; H01L 31/02325
See application file for complete search history.

(56) References Cited

U.S. PATENT DOCUMENTS

| | | | | |
|---|---|---|---|---|
| 5,218,423 A | * | 6/1993 | Kishner | G01B 11/161 356/513 |
| 2005/0073689 A1 | * | 4/2005 | Pang | G01J 11/00 356/450 |
| 2005/0275847 A1 | * | 12/2005 | Moshe | G01J 3/02 356/456 |
| 2006/0215171 A1 | * | 9/2006 | Nakata | G03F 7/70775 356/487 |
| 2008/0037114 A1 | * | 2/2008 | Sheblee | G02B 21/0044 359/385 |
| 2010/0290127 A1 | * | 11/2010 | Kessler | G02B 27/0172 359/631 |

* cited by examiner

*Primary Examiner* — Francis M Legasse, Jr.
(74) *Attorney, Agent, or Firm* — Maginot, Moore & Beck LLP

(57) ABSTRACT

A device for emitting electromagnetic radiation includes at least one optical semiconductor element configured to generate electromagnetic radiation, at least one photodiode, and at least one beam splitter. The beam splitter is arranged relative to the optical semiconductor element and the photodiode in such a way that one portion of the electromagnetic radiation generated by the optical semiconductor element passes through the beam splitter and a further portion of the electromagnetic radiation generated by the optical semiconductor element is reflected by the beam splitter and is directed onto the photodiode.

15 Claims, 3 Drawing Sheets

DEVICE FOR EMITTING ELECTROMAGNETIC RADIATION

This application claims priority under 35 U.S.C. §119 to patent application no. DE 10 2013 212 640.9, filed on Jun. 28, 2013 in Germany, the disclosure of which is incorporated herein by reference in its entirety.

BACKGROUND

Devices for emitting electromagnetic radiation are known in diverse configurations. Corresponding devices can be used for a variety of purposes.

By way of example, such a device can be used as a radiation source for spectroscopic purposes. In particular, absorption measurements for determining a concentration of a substance contained in a fluid can be carried out thereby. The correlation—described by Lambert's and Beer's law—between the concentration of a substance that is contained in a fluid and absorbs electromagnetic radiation and the change in the intensity of electromagnetic radiation upon passing through the fluid contained the absorbing substance allows a relatively simple determination of the concentration of a substance contained in a fluid.

A conventional device for emitting electromagnetic radiation that is used for such spectroscopic measurements generally comprises an optical semiconductor element in the form of a light-emitting diode. An emission characteristic, in particular the intensity and distribution, of a light-emitting diode is not temporally and spatially constant over the operating time of the light-emitting diode and is dependent on a multiplicity of ambient conditions.

SUMMARY

The invention relates to a device for emitting electromagnetic radiation, comprising at least one optical semiconductor element by means of which electromagnetic radiation can be generated, at least one photodiode and at least one beam splitter, wherein the beam splitter is arranged relative to the optical semiconductor element and the photodiode in such a way that one portion of the electromagnetic radiation generated by the optical semiconductor element passes through the beam splitter and a further portion of the electromagnetic radiation generated by the optical semiconductor element is reflected by the beam splitter and is directed onto the photodiode.

With knowledge of the respective reflectance and transmittance of the beam splitter in the device according to the invention, the intensity of the electromagnetic radiation generated by the optical semiconductor element can be ascertained by means of that portion of the electromagnetic radiation generated by the optical semiconductor element which is directed onto the photodiode. As a result, changes in the emission characteristic of the optical semiconductor element can be detected and taken into account for the respective purpose for which the device is used. Therefore, optical measurements can be carried out with very high accuracy by means of the device.

The optical semiconductor element can be formed for example as a light-emitting diode (LED) or as a laser diode (LD), in particular as a surface emitter (VCSEL).

According to one advantageous configuration, the beam splitter is designed to direct electromagnetic radiation entering the device onto the photodiode or onto an additional photodiode of the device. Accordingly the device can be used both for emitting electromagnetic radiation and for detecting electromagnetic radiation. If electromagnetic radiation entering the device is directed onto the same photodiode onto which that portion of the electromagnetic radiation generated by the optical semiconductor element which is reflected by the beam splitter is also directed, the electromagnetic radiation generated by the optical semiconductor element is preferably modulated in such a way that the electromagnetic radiations impinging on the photodiode can be distinguished from one another. The electromagnetic radiation entering the device can be influenced, for example, by the interaction of that portion of the electromagnetic radiation generated by the optical semiconductor element which passes through the beam splitter with at least one substance contained in a fluid. The substance can be analyzed as a result.

In accordance with a further advantageous configuration, the device comprises at least one optical lens arranged between the optical semiconductor element and the beam splitter. Advantageously, the optical lens is formed by an arrangement of a multiplicity of microlenses. The optical lens can be formed for concentrating the electromagnetic radiation generated by the optical semiconductor element. In particular, parallel electromagnetic radiation that is directed onto the beam splitter can be generated by means of the optical lens.

A further advantageous configuration provides for the device to comprise a beam splitter body forming the beam splitter wherein the optical lens is formed by the beam splitter body by virtue of the fact that a side surface of the beam splitter body, via which side surface electromagnetic radiation generated by the optical semiconductor element enters the beam splitter body, is formed in an at least partly curved fashion. By virtue of the fact that at least part of a side surface of the beam splitter body, via which side surface electromagnetic radiation generated by the optical semiconductor element enters the beam splitter body, is formed in a curved fashion, an optical lens integrated into the beam splitter body is formed, such that the arrangement of a separate optical lens can be dispensed with. The optical semiconductor element can be adhesively bonded to that side surface of the beam splitter body via which electromagnetic radiation generated by the optical semiconductor element enters the beam splitter body. The beam splitter body can be formed in a cubic fashion. By way of example, the beam splitter body can be formed by two prisms connected to one another.

It is furthermore deemed to be advantageous if the device comprises at least one optical filter. The optical filter can be formed as a long-pass edge filter and/or as a short-pass edge filter. Specific wavelength ranges of the electromagnetic radiation generated by the optical semiconductor element and/or of the electromagnetic radiation entering the device can thereby be filtered out in order to be able to optimally adapt the device to the respective application.

In accordance with a further advantageous configuration, the components of the device are connected to one another in an immobile fashion. Preferably, the components of the device are jointly molded into a material. As a result, the device acquires a robust and compact design. By virtue of the immobile connection of the components of the device to one another, the device can be used immediately, without a subsequent calibration of the device or an alignment of individual components relative to one another having to be performed on site. The handleability of the device is greatly simplified as a result.

The invention furthermore relates to a system for detecting at least one substance contained in a fluid, comprising at least one device for emitting electromagnetic radiation and at least one optical detector unit, characterized in that the device is formed according to one of the abovementioned configurations or any desired combination thereof. The advantages mentioned above with regard to the device are associated therewith.

The system can be used for detecting substances in gases and/or liquids. By way of example, the system can be used as an exhaust-gas sensor. Furthermore, the system can be used for example for detecting substances contained in a fluid in medical technology, in respiration gas analysis, in fire detection, in lab-on-a-chip applications, in ventilation systems, in climate control and in devices appertaining to consumer electronics such as, for example, in smartphones, in games consoles or the like.

According to one advantageous configuration, the optical detector unit is formed by at least one photodiode of the device. Accordingly, a separate optical detector unit is not required.

A further advantageous configuration provides for the system to comprise at least one electronic evaluation unit which is connected to the at least one optical semiconductor element of the device and/or the optical detector unit in terms of communication technology. By means of the electronic evaluation unit, the optical semiconductor element can be controlled or the properties of the electromagnetic radiation generated by the optical semiconductor element can be influenced. Furthermore, the electronic evaluation unit can be connected to the at least one photodiode of the device in terms of communication technology in order to be able to detect the intensity and type of that portion of the electromagnetic radiation generated by the optical semiconductor element which is reflected by the beam splitter or of the electromagnetic radiation entering the device. As a result of the temporal correlation of the electromagnetic radiation impinging on the at least one photodiode of the device and/or the optical detector unit, the propagation time of a light beam that is emitted by the device and enters the device again and, as a result, the length of the path covered by the light beam can be determined by means of the electronic evaluation unit. A path distance determined in this way can be used for example for determining the absorption in accordance with Lambert's and Beer's law.

Advantageously, the electronic evaluation unit controls the at least one optical semiconductor element of the device in such a way that a modulated electromagnetic radiation can be generated by means of the optical semiconductor element. This is advantageous particularly if a device comprising only one photodiode is used, onto which both that portion of the electromagnetic radiation generated by the optical semiconductor element which is reflected by the beam splitter and at least one portion of the electromagnetic radiation entering the device are directed. Furthermore, a corresponding radiation modulation is advantageous if the device comprises two or more optical semiconductor elements by means of which in each case an electromagnetic radiation can be generated. As a result of a different modulation of the individual electromagnetic radiations the electromagnetic radiations can be distinguished by means of the at least one photodiode of the device and/or a separate optical detector unit and by means of the electronic evaluation unit.

In accordance with a further advantageous configuration, the system comprises at least one reflective unit which is arranged relative to the beam splitter of the device in such a way that the electromagnetic radiation that passes through the beam splitter is directed onto the reflective unit and that the electromagnetic radiation reflected by the reflective unit is directed onto the beam splitter.

It is furthermore deemed to be advantageous if the system comprises at least one optical fiber which is directly connected to the device. As a result, the electromagnetic radiation generated by the device and/or the electromagnetic radiation entering the device can be guided in a targeted manner in order to be able to optimally adapt the system to the respective application.

Preferably, the material from which the optical fiber is formed has the same refractive index as the material into which the components of the device are jointly molded. As a result, differences between the optical properties of the device and of the fiber can be avoided, as a result of which a maximum efficiency of coupling into the optical fiber and out of the latter is ensured.

The invention furthermore relates to a system for measuring the distance between two points in space, comprising at least one device for emitting electromagnetic radiation that is arranged at one of the points, at least one optical detector unit and at least one electronic evaluation unit which is connected to the device and/or the optical detector unit in terms of communication technology, wherein the electronic evaluation unit is designed to determine the length of a path covered by electromagnetic radiation that is emitted by the device and enters the device again or impinges on the optical detector unit by means of a temporal correlation of the electromagnetic radiation that enters the device or impinges on the optical detector unit with the electromagnetic radiation emitted by the device, characterized in that the device is formed according to any of the abovementioned configurations or any desired combination thereof. The advantages mentioned above with regard to the device are associated therewith.

From the temporal correlation of the electromagnetic radiation entering the device or impinging on the optical detector unit with the electromagnetic radiation emitted by the device, firstly it is possible to deduce the propagation time of the electromagnetic radiation in order to determine therefrom the length of the path covered. The second point, at which the device is not arranged, can be formed by any object at which the electromagnetic radiation emitted by the device is at least partly reflected. By way of example, the object can be a house wall or the like.

BRIEF DESCRIPTION OF THE DRAWINGS

The invention is explained by way of example below on the basis of preferred exemplary embodiments with reference to the appended figures, wherein the features presented below both respectively by themselves and in different combinations with one another can constitute an aspect of the invention. In the figures.

DETAILED DESCRIPTION

Figure 1:
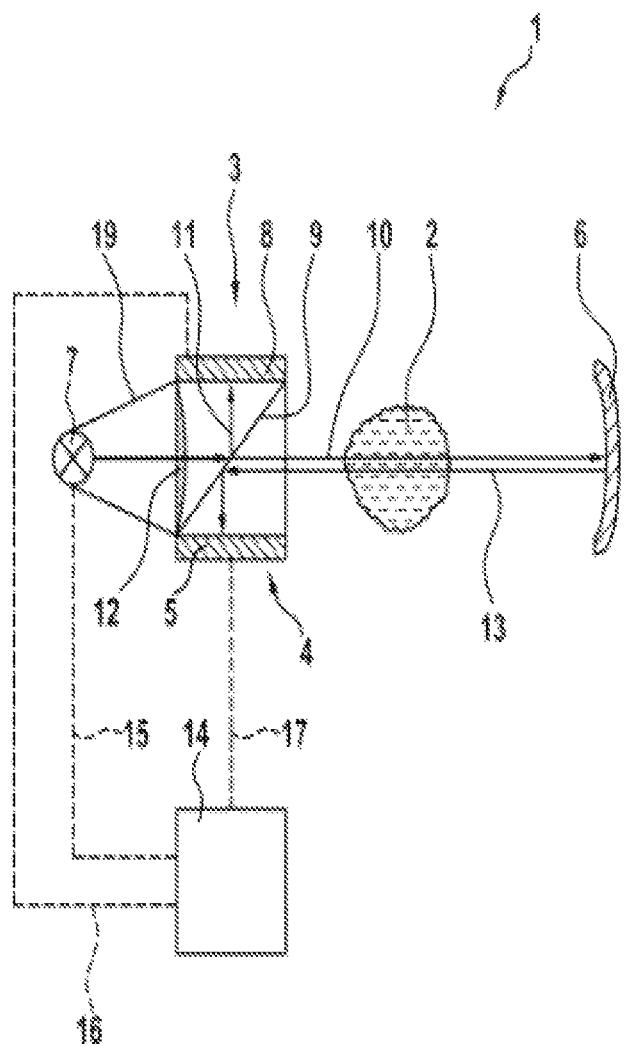
FIG. 1 shows a schematic illustration of one exemplary embodiment of a system according to the invention.

FIG. 1 shows a schematic illustration of one exemplary embodiment of a system 1 according to the invention for detecting a substance contained in a fluid 2. The system 1 comprises at least one device 3 for emitting electromagnetic radiation 19 and at least one optical detector unit 4. The optical detector unit 4 is formed by at least one photodiode 5 of the device 3. Furthermore, the system 1 comprises a reflective unit 6 in the form of a concave mirror and an electronic evaluation unit 14, which is connected to the device 3 in terms of communication technology.

The device 3 comprises an optical semiconductor element 7 by means of which electromagnetic radiation 19 can be generated and which is formed as a light-emitting diode. Furthermore, the device 3 comprises two photodiodes 5 and 8, a beam splitter 9 and an optical lens 12 arranged between the optical semiconductor element 7 and the beam splitter 9. The components 5, 7, 8, 9 and 12 of the device 3 are connected to one another in an immobile fashion. The electronic evaluation unit 14 is connected in terms of communication technology to the optical semiconductor element 7 via a control connection 15 and to the photodiodes 5 and 8 via evaluation connections 16 and 17.

The beam splitter 9 is arranged relative to the optical semiconductor element 7 and the photodiodes 5 and 8 in such a way that one portion 10 of the electromagnetic radiation 19 generated by the optical semiconductor element 7 passes through the beam splitter 9 and a further portion 11 of the electromagnetic radiation 19 generated by the optical semiconductor element 7 is reflected by the beam splitter 9 and directed onto the photodiode 8. By way of example, the portion 10 is approximately 90% and the portion 11 is approximately 10% of the electromagnetic radiation 19 generated by the optical semiconductor element 7. The beam splitter 9 is furthermore designed to direct electromagnetic radiation 13 entering the device 3 onto the additional photodiode 5 of the device 3.

The reflective unit 6 is arranged relative to the beam splitter 9 of the device 3 in such a way that the electromagnetic radiation 10 passing through the beam splitter 3 is directed onto the reflective unit 6 and that the electromagnetic radiation 13 reflected by the reflective unit 6 is directed onto the beam splitter 9.

Figure 2:
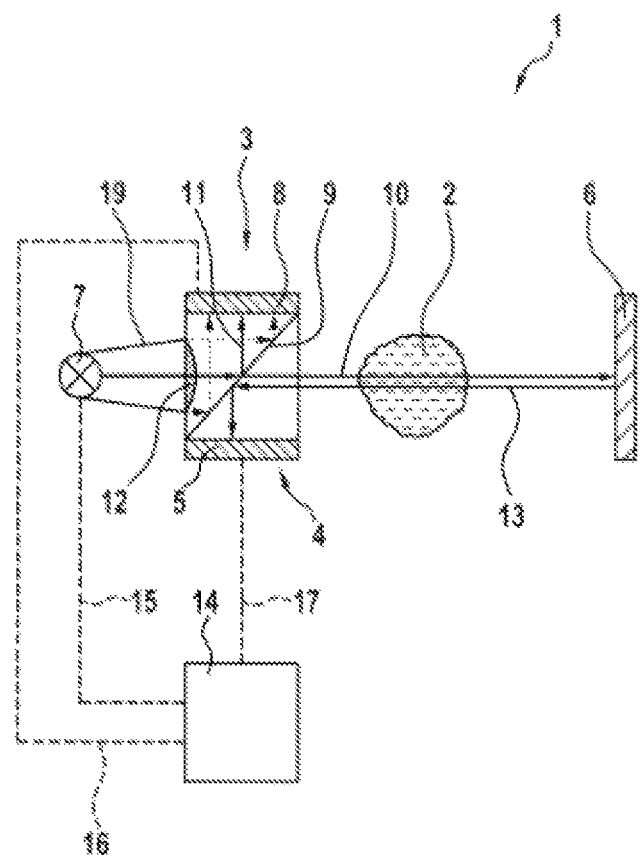
FIG. 2 shows a schematic illustration of a further exemplary embodiment of a system according to the invention.

FIG. 2 shows a schematic illustration of a further exemplary embodiment of a system 1 according to the invention. One difference with respect to the exemplary embodiment shown in FIG. 1 is that the reflective unit 6 is not formed as a concave mirror, but rather as a plane mirror. One essential difference with respect to the exemplary embodiment shown in FIG. 1 is that the cross section of the parallel beam path produced by the optical lens 12 is smaller than the sensor areas of the photodiodes 5 and 8, such that the portion 11 of the electromagnetic radiation 19 generated by the optical semiconductor element 7 which is reflected by the beam splitter 9 impinges only on a central region of the sensor area of the photodiode 8, in which region the photodiode 8 is usually formed in a more sensitive fashion.

Figure 3:
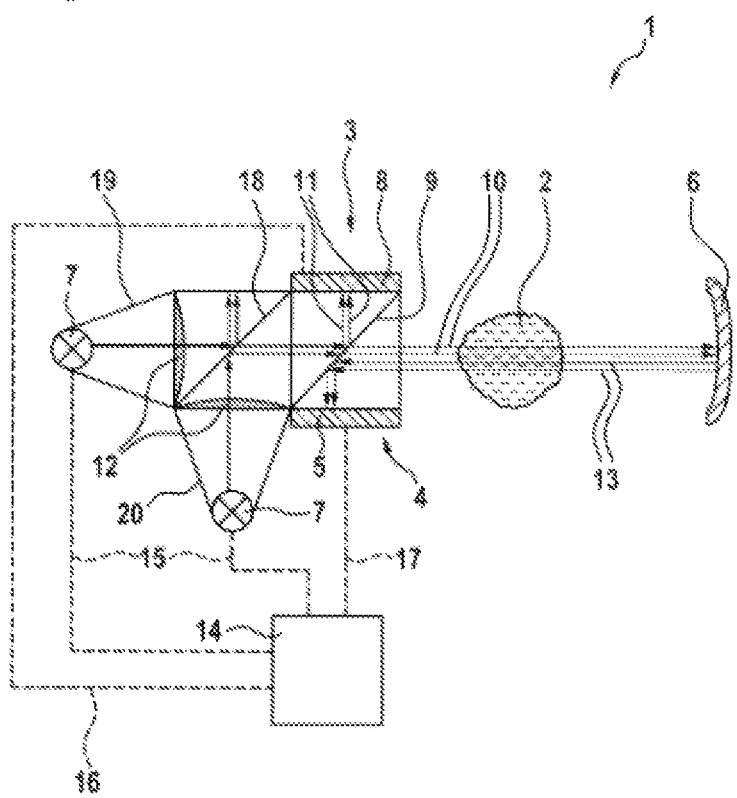
FIG. 3 shows a schematic illustration of a further exemplary embodiment of a system according to the invention.

FIG. 3 shows a schematic illustration of a further exemplary embodiment of a system 1 according to the invention. This exemplary embodiment differs from the exemplary embodiment shown in FIG. 1 in that the device 3 comprises two optical semiconductor elements 7 in the form of light-emitting diodes and that a further beam splitter 18 is provided, via which the electromagnetic radiations 19 and 20 generated by the optical semiconductor elements 7 are guided onto the beam splitter 9, a further optical lens 12 being assigned to the second optical semiconductor element 7.

What is claimed is:

1. A device for emitting electromagnetic radiation, comprising:
   at least one optical semiconductor element configured to generate electromagnetic radiation;
   a photodiode;
   at least one beam splitter, the beam splitter being arranged relative to the optical semiconductor element and the photodiode in such a way that (i) one portion of the electromagnetic radiation generated by the optical semiconductor element passes through the beam splitter and exits the device, and (ii) a further portion of the electromagnetic radiation generated by the optical semiconductor element is reflected by the beam splitter directly onto the photodiode; and
   at least one optical lens arranged between the optical semiconductor element and the beam splitter,
   wherein the beam splitter is formed by a beam splitter body and the optical lens is formed by the beam splitter body by a side surface of the beam splitter body, via which side surface electromagnetic radiation generated by the optical semiconductor element enters the beam splitter body, being formed in an at least partly curved fashion.

2. The device according to claim 1, wherein the beam splitter is configured to direct electromagnetic radiation entering the device from outside the device onto an additional photodiode within the device.

3. The device according to claim 1, wherein the optical lens is formed by an arrangement of a multiplicity of microlenses arranged to provide a parallel beam path to be reflected onto the photodiode.

4. The device according to claim 1, further comprising at least one optical filter.

5. The device according to claim 1, wherein the components of the device are connected to one another in an immobile fashion.

6. The device according to claim 4, wherein the optical filter is formed as one or more of a long-pass edge filter and a short-pass edge filter.

7. The device according to claim 5, wherein the components of the device are jointly molded into a material.

8. A system for detecting at least one substance contained in a fluid, comprising:
   at least one optical detector unit; and
   at least one device configured to emit electromagnetic radiation, the device including:
   at least one optical semiconductor element configured to generate the electromagnetic radiation;
   a photodiode separate from the at least one optical detector;
   at least one beam splitter, the beam splitter being arranged relative to the optical semiconductor element and the photodiode in such a way that (i) one portion of the electromagnetic radiation generated by the optical semiconductor element to be directed to said at least one optical detector unit passes through the beam splitter and exits the device, and (ii) a further portion of the electromagnetic radiation generated by the optical semiconductor element is reflected by the beam splitter directly onto the photodiode and
   at least one optical lens arranged between the optical semiconductor element and the beam splitter,
   wherein the beam splitter is formed by a beam splitter body and the optical lens is formed by the beam splitter body by a side surface of the beam splitter body, via which side surface electromagnetic radiation generated by the optical semiconductor element enters the beam splitter body, being formed in an at least partly curved fashion.

9. The system according to claim 8, wherein the optical detector unit is formed by another photodiode within the device.

10. The system according to claim 8, further comprising at least one electronic evaluation unit connected to one or more of the device and the optical detector unit in terms of communication technology.

11. The system according to claim 8, further comprising at least one reflective unit arranged relative to the beam splitter of the device in such a way that the portion of the electromagnetic radiation generated by the optical semiconductor element that passes through the beam splitter and exits the device is directed onto the reflective unit and that the electromagnetic radiation reflected by the reflective unit is directed onto the beam splitter.

12. The system according to claim 8, further comprising at least one optical fiber directly connected to the device.

13. The system according to claim 10, wherein the electronic evaluation unit controls the at least one optical semiconductor element of the device in such a way that a modulated electromagnetic radiation is configured to be generated by the optical semiconductor element.

14. The system according to claim 12, wherein;
the components of the device are jointly molded into a material; and
the material from which the optical fiber is formed has the same refractive index as the material into which the components of the device are jointly molded.

15. A system for measuring the distance between two points in space, comprising:
at least one device configured to emit electromagnetic radiation that is arranged at one of the points, the device including:
at least one optical semiconductor element configured to generate the electromagnetic radiation;
a photodiode; and
at least one beam splitter, the beam splitter being arranged relative to the optical semiconductor element and the photodiode in such a way that (i) one portion of the electromagnetic radiation generated by the optical semiconductor element passes through the beam splitter and exits the device, and (ii) a further portion of the electromagnetic radiation generated by the optical semiconductor element is reflected by the beam splitter directly onto the photodiode;
at least one optical detector unit separate from the photodiode;
at least one electronic evaluation unit connected to one or more of the device and the optical detector unit in terms of communication technology, the electronic evaluation unit being configured to determine the length of a path covered by electromagnetic radiation that is emitted by the device and exits the device, and then enters the device again or impinges on the optical detector unit, by a temporal correlation of the electromagnetic radiation that enters the device or impinges on the optical detector unit with the electromagnetic radiation emitted by the device;
and
at least one optical lens arranged between the optical semiconductor element and the beam splitter,
wherein the beam splitter is formed by a beam splitter body and the optical lens is formed by the beam splitter body by a side surface of the beam splitter body, via which side surface electromagnetic radiation generated by the optical semiconductor element enters the beam splitter body, being formed in an at least partly curved fashion.

* * * * *